United States Patent [19]

Chan

[11] 4,351,839
[45] Sep. 28, 1982

[54] FUNGICIDAL 2-ARYL-2-1-H-AZOYL-(ALKYL)-GAMMA-BUTYROLACTONES

[75] Inventor: Hak-Foon Chan, Doylestown, Pa.

[73] Assignee: Rohm and Haas Company, Philadelphia, Pa.

[21] Appl. No.: 249,250

[22] Filed: Mar. 30, 1981

[51] Int. Cl.³ .................... A01N 43/64; A01N 43/50; C07D 405/04; C07D 405/06
[52] U.S. Cl. .................... 424/269; 424/245; 424/273 R; 548/101; 548/262; 548/336; 549/295; 549/313; 549/323; 549/324
[58] Field of Search ............ 548/336, 262, 101; 424/273 R, 269, 245

[56] References Cited

U.S. PATENT DOCUMENTS 3,927,018 12/1975 Houlihan ..................... 548/336

OTHER PUBLICATIONS

Jones, J., et al., Can. J. Chem., 48, 1574 (1970).
Chemical Abstracts, 86:29811b (1977) [German OLS No. 2,602,770, Heeres, 7/29/76].
Chemical Abstracts, 90:152419q (1979) [Voigtlaender, H., et al., Arch. Pharm. 1978, 311(11), 927].

Primary Examiner—Richard A. Schwartz
Attorney, Agent, or Firm—Alex R. Sluzas

[57] ABSTRACT

This invention relates to 2-aryl-2-1-H-azoyl-(alkyl)gamma-butyrolactone of the formula:

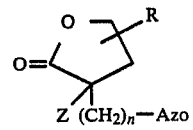

wherein
Z is optionally substituted aryl;
R is hydrogen, alkyl, alkenyl, alkynyl, optionally substituted aryl or optionally substituted aralkyl;
Azo is 1-H-imidiazoyl, 1-H-1,2,4-triazoyl or 4-H-1,2,4-triazoyl;
n is zero or an integer from 1 to 5, and the agronomically acceptable acid addition salts and metal salt complexes thereof, methods for their preparation and their use as pesticides.

9 Claims, No Drawings

FUNGICIDAL 2-ARYL-2-1-H-AZOYL-(ALKYL)-GAMMA-BUTYROLACTONES

BACKGROUND OF THE INVENTION

It has been reported in the literature that 2-phenyl-gamma-butyrolactone was isolated as a metabolite of glutethimides, phenobarbital or pyrimidone in human urine. This compound is also reported to have been synthesized in a 37% overall yield starting with diethylphenylmalonate, sodium hydride and 1,2-dibromoethane. The 2-aryl-2-azoyl(alkyl)gamma-butyrolactones of the present invention are novel compounds as are their methods of preparation and use as pesticides.

SUMMARY OF THE INVENTION

This invention relates to gamma-butyrolactones of Formula (I) wherein Z is aryl or substituted aryl; R is hydrogen, ($C_1$ to $C_{10}$) alkyl, ($C_3$ to $C_8$)alkenyl; ($C_3$ to $C_8$)alkynyl, aryl or substituted aryl or aryl ($C_1$ to $C_4$)alkyl, the aryl portion of which may be substituted with up to three substituents; Azo is 1-$\underline{H}$-imidazoyl, 1-$\underline{H}$-1,2,4-triazoyl, or 4-$\underline{H}$-1,2,4-triazoyl; n is zero or an integer from 1 to 5 and the agronomically acceptable acid addition salts and metal salt complexes thereof.

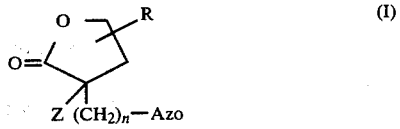

This invention also relates to methods for preparing these compounds and their use in controlling phytopathogenic fungi such as barley net blotch (*Helminthosporium teres*), broad bean chocolate spot (*Botrytis fabae*), bean powdery mildew (*Erysiphe polygoni*), grape downy mildew (*Plasmopora viticola*), rice blast (*Piricularia oryzae*), peanut leaf spot (*Cercospora arachidicola*) tomato late blight (*Phytophthora infestans*) and wheat stem rust (*Puccinia graminis* f. sp. *tritici* race 15B-2).

The term "alkyl", "alkenyl" and "alkynyl" as utilized in the definition of the substituent R and the appended claims is meant to include an alkyl, alkenyl or alkynyl group of up to ten carbon atoms which may be a branched or straight chain group. Examples of "alkyl" include methyl, ethyl and propyl. The term "aryl" as utilized in the definition of the substituent R and Z in the specification and the appended claims means a phenyl or naphthyl group, preferably a phenyl group. "Substituted aryl" means an aryl group substituted with up to three substituents, preferably up to two substituents, selected from the group consisting of halogen, nitro, trihalomethyl, cyano, ($C_1$ to $C_4$)alkyl, ($C_1$ to $C_4$)alkoxy, ($C_1$ to $C_4$)alkylthio, ($C_1$ to $C_4$)alkylsulfinyl, ($C_1$ to $C_4$)alkylsulfonyl or phenyl, benzyl, phenoxy, phenylthio, phenylsulfinyl or phenylsulfonyl, the phenyl portion of which may be substituted with the above substituents. The term "aralkyl" as utilized in the definition of the substituent R in this specification and the appended claims is meant to include aralkyl groups wherein the "aryl" portion is as defined above, and the alkyl portion is an alkyl group of up to 4 carbon atoms which may be a branched or straight chain group.

Among the agronomically acceptable acids which can be utilized in making the acid addition salts of this invention are hydrochloric, hydrobromic, nitric, sulfuric, phosphoric, hydroiodic, hydrofluoric, perchloric, p-toluenesulfonic, methanesulfonic, acetic, citric, tartaric, malic, maleic, oxalic, fumaric, benzoic, phthalic and the like.

Among the agronomically acceptable metal salts having the Formula (MY) which can be utilized in making the metal salt complexes of this invention are metal salts wherein the metal cation (M) is selected from Groups IIA, IB, IIB, VIB, VIIB and VIII of the Periodic Table and the anion (Y) is a counterion selected in such a manner that the sum of the valence charges of the cation M and the anion X equals zero.

Typical cations (M) of the metal salt complexes of this invention are magnesium, manganese, copper, nickel, zinc, iron, cobalt, calcium, tin, cadmium, mercury, chromium, lead, barium and the like.

Typical anions (Y) of the metal salt complexes of this invention are chloride, bromide, iodide, fluoride, sulfate, bisulfate, perchlorate, nitrate, nitrite, phosphate, carbonate, bicarbonate, acetate, citrate, oxalate, tartarate, malate, maleate, fumarate, p-toluenesulfonate, methanesulfonate, (mono) (di) ($C_1$ to $C_4$) alkyldithiocarbamate, ($C_1$ to $C_4$) alkylene-bis-dithiocarbamate and the like.

A preferred embodiment of this invention relates to compounds according to Formula I wherein Z is phenyl or phenyl substituted with up to two halogen atoms: R is a ($C_1$ to $C_4$)alkyl group; Azo is a 1-$\underline{H}$-imidazoyl or 1-$\underline{H}$-1,2,4-triazoyl group and n is zero or the integer 1.

A more preferred embodiment of this invention relates to compounds according to Formula I where Z is phenyl or 2,4-dichlorophenyl; R is methyl or ethyl; Azo is 1-$\underline{H}$-imidazoyl or 1-$\underline{H}$-1,2,4-triazoyl; and n is zero or the integer 1.

Typical compounds encompassed by the present invention include:
4-n-propyl-2-(1-$\underline{H}$-imidazoyl)-2-phenyl-gamma-butyrolactone;
4-ethyl-2-(1-$\underline{H}$-imidazoyl)-2-(4-chlorophenyl)-gamma-butyrolactone;
4-methyl-2-(1-$\underline{H}$-imidazoyl)-2-(2-chloro-4-fluorophenyl)-gamma-butyrolactone;
4-isopropyl-2-(1-$\underline{H}$-imidazoyl)-2-(3,4-dibromophenyl)-gamma-butyrolactone;
4-n-propyl-2-(1-$\underline{H}$-imidazoyl)-2-(3,5-diiodophenyl)-gamma-butyrolactone;
4-n-butyl-2-(1-$\underline{H}$-imidazoyl)-2-(2,3-dinitrophenyl)-gamma-butyrolactone;
4-n-hexyl-2-(1-$\underline{H}$-imidazoyl)-2-(4-trifluoromethylphenyl)-gamma-butyrolactone;
4-iso-heptyl-2-(1-$\underline{H}$-1,2,4-triazoyl)-2-(2-chloro-4-cyanophenyl)-gamma-butyrolactone;
4-n-octyl-2-(1-$\underline{H}$-imidazoylmethyl)-2-(3-cyanophenyl)-gamma-butyrolactone;
4-sec-nonyl-2-(1-$\underline{H}$-1,2,4-triazoylpropyl)-2-(4-chloro-2-methylphenyl)-gamma-butyrolactone;
4-n-decyl-2-(1-$\underline{H}$-imidazoyl)-2-(2,3,5-trimethylphenyl)-gamma-butyrolactone;
4-allyl-2-(1-$\underline{H}$-imidazoylbutyl)-2-(2,4-dimethoxyphenyl)-gamma-butyrolactone;
4-(2-octenyl)-2-(1-$\underline{H}$-imidazoyl)-2-tolylphenyl-gamma-butyrolactone;
4-propargyl-2-(1-$\underline{H}$-1,2,4-triazoylpentyl)-2-(4-anisylphenyl)-gamma-butyrolactone;
4-(2-octynyl)-2-(1-$\underline{H}$-1,2,4-triazoyl)-2-(4-methylthiophenyl)-gamma-butyrolactone;

4-benzyl-2-(1-H-imidazoylmethyl)-2-(4-methylsulfinyl-
  phenyl)-gamma-butyrolactone;
4-phenethyl-2-(1-H-1,2,4-triazoyl)-2-(4-methylsulfonyl-
  phenyl)-gamma-butyrolactone;
and the agronomically acceptable acid addition salts
and metal salt complexes thereof.

For the preparation of general structure (I) when
n=1 to 5, the common intermediate, 3- or 4-substituted
gamma-butyrolactone (III) is required. Compound (III)
is then reacted with a terminal dihaloalkane, like dibro-
momethane, 1,3-dibromopropane and the like, under
strong basic conditions which gives 2-haloalkyl gamma-
butyrolactone (IV), (Eq. 2). The reaction of (IV) with
1-H-imidazole, metal salts of imidazole, 1-H-1,2,4-
triazole or metal salts of 1-H-1,2,4-triazole provides the
expected product (I), (Eq. 3). When 1-H-1,2,4-triazole is
used in the above reaction, a mixture of the 1- and 4-sub-
stituted 1,2,4-triazoyl product (V-VI) is obtained (Eq.
4).

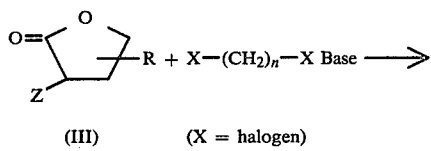

(III)   (X = halogen)

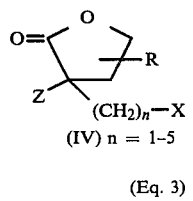

(IV) n = 1–5

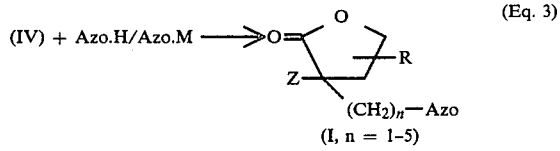

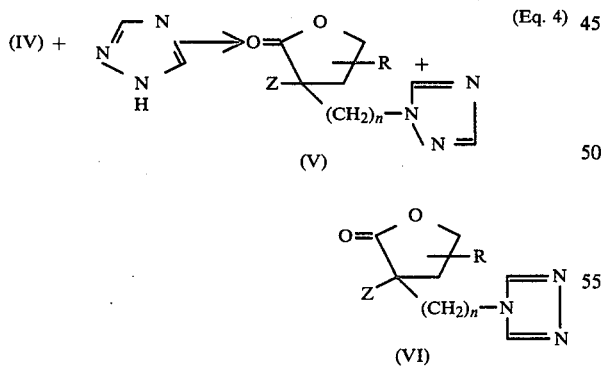

Only a few substituted gamma-butyrolactones (III)
are known in the literature and their synthesis involves
tedious and low yield reactions. As mentioned above,
2-phenyl-gamma-butyrolactone (VII), a metabolite of
glutethimide, phenobarbital and pyrimidone in human
urine, was synthesized in a 37% overall yield starting
with diethylphenylmalonate (VIII), sodium hydride,
and 1,2-dibromoethane, (Eq. 5).

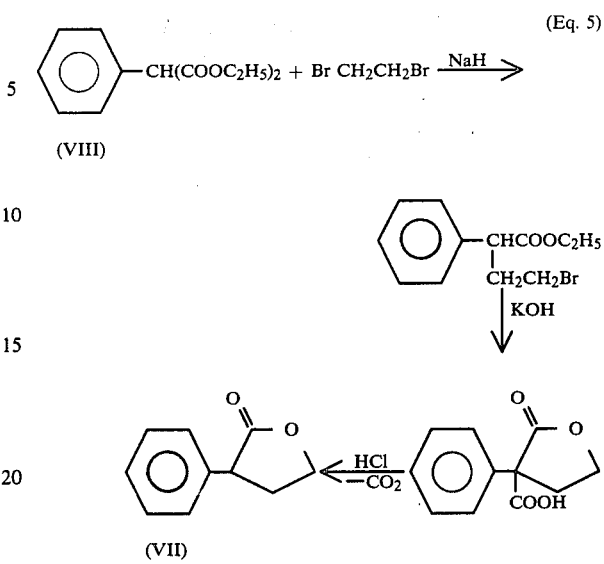

The gamma-butyrolactone of structure (III) may be
prepared from an aryl acetonitrile (IX) and an epoxide
(X). Alkylation of aryl acetonitrile (IX) with epoxide
(X) provides hydroxy cyanide (XI) which under basic
conditions cyclizes to gamma-iminobutyrolactone
(XII). Compound (XII) may then be hydrolyzed to the
desired lactone product (III). (Eq. 6 and 7).

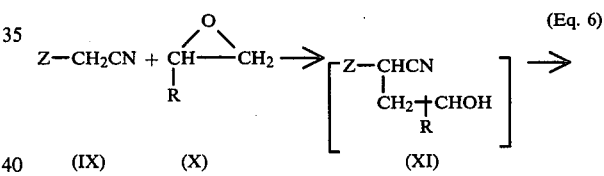

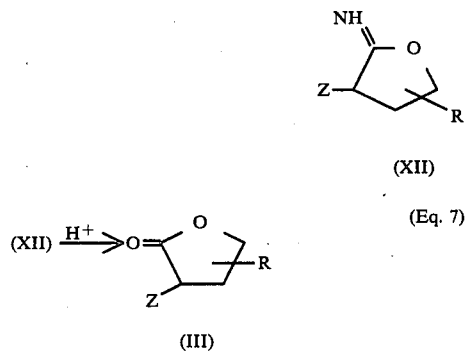

The above synthetic sequence for the preparation of
substituted gamma-butyrolactones is a novel synthetic
approach. A high yield, one-pot procedure has also
been developed.

Compounds of structure (I), when n=0, can also be
prepared from gamma-butyrolactone (III). Bromination
of gamma-butyrolactone (III) with molecular bromine
or N-bromosuccinimide gives alpha-bromo-gamma-
butyrolactone (XIII) which upon reaction with imidaz-
ole or triazole provides the desired azoyl product (I,
n=0). (Eq. 8).

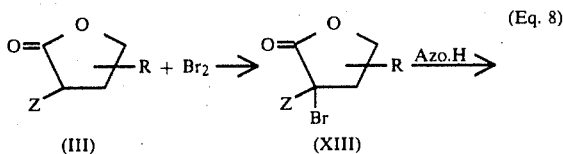

(Eq. 8)

Alternatively, compounds of structure (I), when n=0, can be prepared by reacting an aryl cyano imidazole or triazole of structure (XIV) with an epoxide (x) under basic conditions followed by hydrolysis of the intermediate gamma-iminobutyrolactone (XV) to the desired product (I, n=0) (Eq. 9).

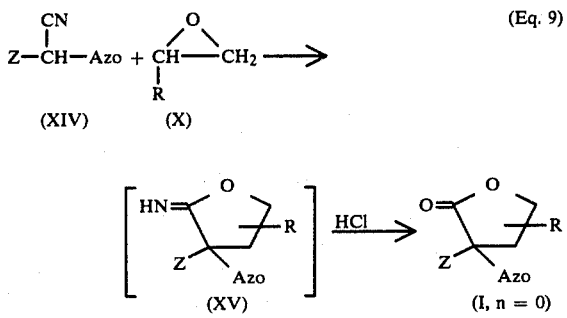

(Eq. 9)

The following examples are provided to illustrate methods for preparing the compounds encompassed by the present invention. These examples are not to be construed in any manner as being limitations of the breadth and scope of this invention.

EXAMPLE 1

Preparation of 3(4)-ethyl-2-(1H-imidazole)-2-phenyl-gamma-butyrolactone

A. Alpha-(1H-imidazole)benzyl cyanide

To a suspension of 40.8 g. (0.6 mole) of 1-H-imidazole, 83 g. (0.6 mole) of potassium carbonate in 250 ml. of acetonitrile is added 98 g. (0.5 mole) of alpha-bromobenzyl cyanide dropwise. The resulting mixture is stirred at 65° C. overnight. Solvent is then evaporated under reduced pressure and the residue is taken up in methylene chloride and washed with water, saturated sodium chloride solution and dried over sodium sulfate. Solvent is evaporated to give 65 g. of a brown oil. This material is further purified by converting it to its nitric acid salt and back neutralizing with diluted ammonium hydroxide solution to give 45 g. of desired product.

nmr (CDCl$_3$): δ6.4 (S, 1H); 6.8–7.7 (m, 8H).

B.

3(4)-ethyl-2-(1H-imidazole)-2-phenyl-gamma-butyrolactone

To a suspension of 12.9 g. (0.12 m) lithium diisopropylamide in 50 ml. tetrahydrofuran is added a solution of 18.3 g. (0.1 m) alpha-(1H-imidazole)benzylcyanide in 50 ml. tetrahydrofuran in ½ hour at −60° C. under nitrogen. The reaction mixture is warmed to −40° C. when a solution of 8.9 g. (0.12 m) 1,2-epoxy butane and 21.5 g. (0.12 m) hexamethylphosphoramide is added dropwise. The temperature is maintained at −40° C. throughout the addition. The reaction mixture is then stirred at room temperature for two days. It is poured into 300 ml of saturated ammonium chloride solution and extracted with ether. The combined ether extracts are dried over sodium sulfate and filtered. The solvent is removed under vacuum to give 6 g of a yellow oil. Analysis of the reaction product by GLC indicates that it is a mixture of two isomers. Further analysis by GC/mass spectrum also indicates that it is a mixture of structural isomers with identical molecular ions corresponding to the expected structure.

nmr (CDCl$_3$): δ1.0 (t, 3H); 1.8 (m, 2H); 3.0 (broad multiplets, 2H); 4.4 (m, 1H); 6.8–7.8 (m, 8H).

EXAMPLE 2

Preparation of 4-ethyl-2-phenyl-2-(1H-imidazolemethyl)-gamma-butyrolactone

A. 4-ethyl-2-phenyl-gamma-butyrolactone

To a mixture of 117 g. (1.0 m) benzyl cyanide, 72 g. (1.1 m) powdered 86% potassium hydroxide and 250 ml. dimethylformamide under a nitrogen atmosphere is added dropwise 74 g. (1.0 m) 1,2-epoxy-butane at 5° C. The temperature is held at 5° C. for 30 minutes and allowed to warm to room temperature. The reaction mixture is poured into 1,500 ml. water and extracted with 5×200 ml. toluene. To the combined toluene extracts is added 50 ml. of 50% hydrochloric acid and the mixture is heated on a steam bath for one hour. The toluene layer is then water washed until it is neutral, dried over sodium sulfate and filtered. The solvent is removed under vacuum to give 135 g. of a pale yellow oil.

B.

2-bromomethyl-4-ethyl-2-phenyl-gamma-butyrolactone

To a solution of 19.4 g. (0.19 m) diisopropylamine in 100 ml. of dry tetrahydrofuran is added dropwise 12.3 g. (0.19 m) n-butyl lithium at −75° C. under nitrogen. Stirring is continued for ½ hour when a solution of 30 g. (0.16 m) 4-ethyl-2-phenyl-gamma-butyrolactone in 50 ml. tetrahydrofuran is added dropwise in one hour. The resulting mixture is further stirred for ½ hour and a mixture of 33 g. (0.19 m) dibromomethane and 34 g. (0.19 m) hexamethylphosphoramide is added dropwise. The reaction temperature is maintained at −75° C. throughout the additions. The reaction mixture is stirred at room temperature overnite. It is then poured into 500 ml. of saturated ammonium chloride solution and extracted with ether. The combined ether extracts are dried over sodium sulfate and filtered. Solvent is removed under vacuum to give 39 g. of an oil which is further purified by bulb-to-bulb vacuum distillation to give 26 g. of pure product.

C.

4-ethyl-2-phenyl-2-(1H-imidazolemethyl)-gamma-butyrolactone

A mixture of 5 g. (0.0177 m) of 2-bromomethyl-4-ethyl-2-phenyl-gamma-butyrolactone, 10 g. (0.15 m) imidazole and 0.5 ml. dimethyl sulfoxide is heated at 120° C. for twenty hours. The crude product is then dissolved in methylene chloride and washed with water. Methylene chloride is evaporated and the crude product is purified by passing through a silica gel column. The impurities are removed with ether and the product is eluted with ethyl acetate. A total of 2.2 g. of pure product is obtained.

nmr: (CDCl$_3$): δ0.8 (t, 3H), 1.4 (m, 2H) 2.5 (m, 2H), 4.0 (m, 1H) 4.4 (q, 2H), 6.7-7.5 (M, 8H).

EXAMPLE 3

Preparation of 2-(2,4-dichlorophenyl)-4-ethyl-2-(1H-imidazolemethyl)-gamma-butyrolactone

A.

2-(2,4-dichlorophenyl)-4-ethyl-gamma-butyrolactone

To a mixture of 186 g. (1 mole) of 2,4-dichlorobenzyl cyanide and 60 g. (1.1 mole) of powdered potassium hydroxide in 400 ml. of dry dimethyl formamide is added 75 g. (1 mole) of 1,2-epoxy butane dropwise at 10° C. The resulting brown reaction mixture is stirred at room temperature overnight. It is then poured into water and extracted with ether. The combined ether extracts are washed with water, 5% sodium chloride solution and dried over magnesium sulfate. Solvent is evaporated to give 228 g. of a brown oil which is assigned the iminolactone structure due to strong ir absorption at 1680 cm$^{-1}$. This material is redissolved in toluene and 300 ml. 25% hydrochloric acid are added. The mixture is heated over a steam bath for two hours. The organic layer is separated and washed with water, saturated sodium chloride solution and dried over magnesium sulfate. Solvent is evaporated to give a light yellow oil which is further purified by vacuum distillation (150° C./0.2 mm) to give 200 g. of desired product.

ir (CHCl$_3$): 1780 cm$^{-1}$ nmr (CDCl$_3$): δ1.0 (t, 3H), 1.3-30 (m, 4H), 4.5 (m, 2H), 7.1-7.6 (m, 3H).

B.

2-bromomethyl-4-ethyl-2-(2,4-dichlorophenyl)-gamma-butyrolactone

To a solution of 14.8 g. (0.23 m) diisopropylamine in 100 ml. of dry tetrahydrofuran is added 14.8 g. (023 m) n-butyllithium at −60° C. under nitrogen. Stirring is continued for 15 minutes when a solution of 50 g. (0.19 m) 2-(2,4-dichlorophenyl)-4-ethyl-gamma-butyrolactone in 75 ml. of tetrahydrofuran is added dropwise in one hour. The resulting mixture is further stirred for an addition ½ hour when the temperature is raised to −40° C. and a solution of 40.3 g. (0.23 m) dibromomethane and 41.5 g. (0.23 m) hexamethylphosphoramide is added dropwise in 45 minutes. The reaction mixture is stirred at room temperature overnight. It is then poured into 500 ml. of saturated ammonium chloride solution and extracted with ether. The combined ether extracts are dried over sodium sulfate and filtered. The solvent is removed under vacuum and the residue is further purified by vacuum distillation (158° C./0.1 mm) to give 47 g. of a yellow oil.

C.

2-(2,4-dichlorophenyl-4-ethyl-2-(1H-imidazolemethyl)-gamma-butyrolactone

A mixture of 9 g. (0.03 m) 2-bromomethyl-4-ethyl 2-(2,4-dichlorophenyl)-gamma-butyrolactone, 10 g. (0.15 m) imidazole and 1 ml. dimethyl sulfoxide is heated at 130° C. for 3 days. The crude is then dissolved in methylene chloride and washed with water. The product is further purified by converting to its hydrochloride salt and then back neutralizing with diluted ammonium hydroxide solution to give 3 g. of pure product.

nmr (CDCl$_3$): δ0.8 (t, 3H), 1.4 (m, 2H), 2.5 (m, 2H), 3.6 (m, 1H), 4.6 (q, 2H), 6.9-7.7 (m, 6H).

EXAMPLE 4

Preparation of 4-ethyl-2-phenyl-2-(1H-1,2,4-triazolemethyl)-gamma-butyrolactone

A mixture of 10 g. (0.0353 m) of 2-bromomethyl-4-ethyl-2-phenyl-gamma-butyrolactone, 15 g. (0.22 m)-1-H-1,2,4-triazole and 0.5 ml. of dimethyl sulfoxide is heated at 165° C. for five days. The crude is then dissolved in methylene chloride and washed with water. Methylene chloride is evaporated and the crude product is purified by passing through a silica gel column. The impurities are removed with ether and the product is eluted with ethyl acetate. A total of 2.8 g. of pure product is obtained, m.p.=112°-114° C.

nmr (CDCl$_3$): δ0.8 (t, 3H), 1.4 (m, 2H), 2.4 (m, 1H), 3.0 (m, 1H), 4.1 (m, 1H), 4.5 (q, 2H), 7.3 (m, 5H), 7.7 (s, 1H), 7.9 (s, 1H).

EXAMPLE 5

Preparation of 2-(2,4-dichlorophenyl)-4-ethyl-2-(1H-1,2,4-triazolemethyl)-gamma-butyrolactone A mixture of 17 g. (0.05 m) 2-bromomethyl-2-(2,4-dichlorophenyl)-gamma-butyrolactone, 20 g. (0.29 m) of 1,2,4-triazole and 1 ml. dimethyl sulfoxide is heated at 170° C. for 3 days. The crude is dissolved in methylene chloride and washed with water. The product is further purified by converting to its hydrochloride salt and then back neutralizing with ammonium hydroxide to the free base to give 1.5 g. of solid, m.p.=99°-101° C.

nmr (CDCl$_3$): δ0.8 (5, 3H), 1.4 (m, 2H), 2.4 (m, 1H), 3.1 (m, 1H), 3.7 (m, 1H), 4.8 (q, 2H), 7.1-7.7 (m, 3H), 7.9 (s, 1H), 8.1 (s, 1H).

The compounds in Tables I and II below were prepared by the procedures given in the above examples. Again, this list of compounds is not to be interpreted as a limitation on the breadth and scope of this invention.

TABLE I $$O=\underset{Z}{\overset{O}{\diagup\!\!\!\diagdown}}\!\!-\!R$$

$(CH_2)_n$—Azo.M

| Ex. No. | Z | R | n | Azo | M |
|---|---|---|---|---|---|
| 1 | C$_6$H$_5$ | 3(4)—C$_2$H$_5$ | 0 | Imidazole | — |
| 2 | C$_6$H$_5$ | 4-C$_2$H$_5$ | 1 | " | — |
| 3 | 2,4-Cl$_2$C$_6$H$_3$ | 4-C$_2$H$_5$ | 1 | " | — |
| 4 | C$_6$H$_5$ | 4-C$_2$H$_5$ | 1 | 1-Triazole | — |
| 5 | 2,4-Cl$_2$C$_6$H$_3$ | 4-C$_2$H$_5$ | 1 | " | — |
| 6 | C$_6$H$_5$ | 4-C$_2$H$_5$ | 1 | Imidazole | HCl |
| 7 | 2,4-Cl$_2$C$_6$H$_3$ | 4-C$_2$H$_5$ | 1 | 1-Triazole | HNO$_3$ |
| 8 | 2,4-Cl$_2$C$_6$H$_3$ | 4-C$_4$H$_9$ | 1 | 1-Triazole | — |

TABLE II

| Ex. No. | MP (°C.) | Elemental Analysis: Cal'd. (Found) | | | | |
|---|---|---|---|---|---|---|
| | | C | H | Cl | N | O |
| 1 | Oil | 70.29 | 6.29 | — | 10.93 | 12.48 |
| | | (69.72) | (6.64) | — | (10.88) | (13.04) |
| 2 | " | 71.09 | 6.71 | — | 10.36 | 11.84 |

TABLE II-continued

| Ex. No. | MP (°C.) | Elemental Analysis: Cal'd. (Found) | | | | |
|---|---|---|---|---|---|---|
| | | C | H | Cl | N | O |
| 3 | " | (71.25) 56.65 (56.47) | (6.85) 4.75 (5.09) | — 20.90 (20.31) | (10.75) 8.26 (8.87) | (12.15) 9.43 |
| 4. | 112-114 | 66.40 (65.58) | 6.32 (6.36) | — — | 15.49 (15.45) | 11.79 (12.42) |
| 5 | 99-101 | 52.96 (52.83) | 4.44 (4.22) | 20.84 (20.36) | 12.35 (12.81) | 9.41 10.10 |
| 6. | 88-95 | 62.64 (61.02) | 6.24 (6.51) | 11.56 (11.60) | 9.13 (9.04) | 10.43 (11.69) |
| 7. | 106-9 | 44.68 (44.74) | 4.00 (3.93) | 17.58 (15.56) | 13.89 (13.37) | — — |
| 8. | Oil | identified by nmr and mass spectra, m/e = 368 | | | | |

The gamma-butyrolactone of this invention are highly effective broad spectrum phytopathogenic fungicides which are effective at rates of up to 2000 ppm in controlling agronomically important fungi such as barley net blotch (*Helminthosporium terres*) on barley plants, bean powdery mildew (*Erysiphe polygoni*) on bean plants, rice blast (*Piricularia oryzae*) on rice plants, tomato late blight (*Phytophthora infestans*) on tomato seedlings, wheat stem rust (*Puccinia graminis* f. sp. *tritici* race 15B-2) on wheat seedlings and cercospora leafspot (*Cercospora arachidicola*) on peanut plants.

The following test procedures are followed when candidate compounds are initially evaluated for activity against varied plant pathogenic organisms. These compounds are weighed into 30 mg. aliquots and diluted with 100 cc. solvent. This provides an application rate of 300 ppm to plant foliage. The candidate compounds are applied on overhead mechanical sprayer at a speed setting of 2.3 and 60 psi air pressure. Plant foliage is treated by one overhead vertical fan nozzle (T-Jet No. 6501; No. 225 core) and two 45° horizontal nozzles (¼ NN, No. 2 tip, No. 215 core).

The following disease rating scale was used for evaluating these fungicidal agents.

```
A = 97-100% disease control
B = 90-96% disease control
C = 70-80% disease control
D = 50-69% disease control
E = <50% disease control
```

$$\% \text{ Disease Control} = \frac{\text{disease of untreated} - \text{disease of treated}}{\text{disease of untreated}} \times 100$$

The following Examples A through H describe the procedures used to evaluate the activity of the compounds of this invention against various phytopathogenic fungi.

EXAMPLE A

Rice Blast (*Piricularia oryzae*) (RB)

Rice plants (var. Nato) are trimmed to a height of approximately 5 inches, 24 hours prior to chemical application. This procedure provides plants of uniform height and permits rapid inoculation of treated plants.

*Piricularia oryzae* is cultured on rice polish agar (RPA) plates for 14 days at ambient temperature and normal room light intensity. Spores are harvested by adding deionized water containing 2 g. gelatin and 0.5 g. sodium oleate per liter to the RPA plates and scraping the agar surface with a rubber policeman or other similar blunt object. The spore suspension is filtered through cheesecloth to remove mycelial and agar fragments and then adjusted to a concentration of $7.510 \times 10^5$ spores/ml.

Rice plants are inoculated by spraying the leaves and stems with an air brush until a uniform film of inoculum is observed on the leaves. The inoculated plants are incubated in a humid environment (75°-85° F.) for 24 hours prior to being placed in a greenhouse environment.

Treatment comparisons are made 7-8 days after inoculation. Initial race blast lesions appear as small brown necrotic spots on the foliage. The typical lesion is eliptical, 1-2 cm long with a large necrotic gray center and brown margins.

EXAMPLE B

Bean Powdery Mildew (*Erysiphe polygoni*) (BPM)

Bean plants (var. Dwarf Hort) are thinned to two plants per pot 24 hours prior to chemical application.

*Erysiphe polygoni* is cultured on bean leaves for 10-21 days under existing greenhouse conditions. Spores are harvested by adding deionized water containing 0.5 ml. of Tween 80 per 500 ml. water to a quart jar containing excised mildew infected bean leaves. The spores are loosened from the leaf surface by shaking the jar. The resulting suspension is filtered through cheesecloth to remove plant debris and adjusted to $2-2.5 \times 10^5$ spores per ml.

Bean plants are inoculated by spraying the leaves and stems with inoculum until a uniform film of inoculum is observed on the plant. Inoculated plants are maintained under existing greenhouse conditions.

Treatment comparisons are made 8-10 days after inoculation. Typical bean powdery mildew signs are circular white mycelial mats (fructifications) on the leaf surface.

EXAMPLE C

Broad Bean Gray Mold Leaf Spot (*Botrytis fabae*) (BOT)

Broad bean (*Vicia faba*) are trimmed to a height of approximately 4½ inches, 24 hours prior to chemical application. This procedure provides plants of a uniform height and permits rapid and uniform inoculation of treated plants.

*Botrytis fabae* is cultured on oatmeal agar (OA) slants for 21 days at ambient temperature and low light intensity. Spores are harvested by adding deionized water to the OA slants and scraping the agar surface with a rubber policeman or similar blunt object. The spore suspension is filtered through a cheesecloth to remove mycelial and agar fragments and then adjusted to a concentration of $1.75-2.0 \times 10^5$ spores per ml. with an inoculation medium. The inoculation medium (20 gms. potassium nitrate, 10 mgm ascorbic acid, 1500 ml. deionized water and 500 ml. apple juice) is to provide improved spore germination on the surface of the broad bean leaves and stems.

Broad bean plants are inoculated by spraying the foliage with the fungicide group's overhead mechanical sprayer. Inoculated plants are incubated in a humid environment at 70°-75° F. for 66 hours.

Treatment comparisons are made 66-68 hours after inoculation. Typical broad bean chocolate leaf spot symptoms appear as regular circular to lanceolate lesions on plant leaves and stems.

EXAMPLE D

Grape Downy Mildew (*Plasmopora viticola*) (GDM)

Grape seedlings 4-5 inches tall are used.

*Plasmopora viticola* is cultured on grape leaves for 7 days at 65°-75° C. in a growth room at moderate light intensity. Spores are harvested by adding deionized water and scraping the leaf surface with a camels hair brush. The spore suspension is filtered through cheesecloth to remove plant debris and adjusted to a concentration of $1-1.25 \times 10^6$ spores per ml.

The grape plants are inoculated by spraying the leaves with a hand held air brush until small uniform droplets of inoculum are observed on the leaves. The inoculated plants are incubated in a humid environment at 65°-70° F. for 48 hours prior to being placed in a growth room.

Treatment comparisons are made 7 days after inoculation. Typical grape downy mildew symptoms appear on the upper leaf surface as pale-yellow spots variable in size and form, frequently circular without a distinct line of demarcation. Under humid conditions the lower leaf surface is covered by conspicuous fungal growth.

EXAMPLE E

Wheat Stem Rust (*Puccinia graminis* f. sp. *tritici* race 15B-2 (WSR)

Seven-day-old wheat plants (var. Wanser) are trimmed to approximately $2\frac{1}{2}$ inches, 24 hours prior to chemical application to provide a uniform plant height and to facilitate uniform inoculation.

Wheat stem rust is cultured on wheat seedlings (var. Wanser) for a period of 14 days under existing greenhouse conditions.

A spore suspension of *Puccinia graminis* f. sp. *tritici race* 15B-2 is made by excising infected wheat leaves and placing the leaves into a pint jar containing water and the surfactant. "Tween 80" (1 drop. 100 cc.). The surfactant serves to free the rust urediospores from the sori and improves inoculum retention when applied to plant foliage. The resulting spore suspension is filtered through cheesecloth to remove the leaves and assorted other plant debris. The spore concentration is not adjusted, but a minimum of $2.5\times10^5$ spores per ml. are required to obtain an acceptable disease level.

Wheat plants are inoculated by applying the stem rust spore suspension until run-off with a DeVilbiss atomizer at 5 psi air pressure. After inoculation, the plants are placed into a humid environment at approximately 68° C. A timer is used to permit 12 hours of continuous darkness followed by a minimum of 3-4 hours of light with an intensity of 500 ft. candles. The temperature in the chamber should not exceed 85° F. At the end of the light period, the fogger is turned off and vented to allow the plants to dry slowly prior to being placed into a greenhouse environment.

The plants are permitted to grow under greenhouse conditions for a period of 2 weeks prior to making treatment comparisons. Wheat stem rust is characterized by brick red spores in irregularly shaped sori on the leaves and stems of the wheat seedlings.

EXAMPLE F

Tomato Late Blight (*Phytophthora infestans*) (TLB)

Tomato (var. Rutgers) seedlings, 2½-3 inches tall, are fertilized with a water soluble fertilizer 4-5 days prior to chemical application to promote rapid succulent growth and better symptom expression.

The pathogen is grown on lima bean agar for 12-15 days at 60° F. and the fungal growth is removed by the agitation of a rubber policeman on a glass rod over the surface of the agar in the presence of deionized water. The inoculum is strained through cheesecloth to remove mycelial and agar fragments and the spore concentration adjusted to $5-6\times10^5$ spores/ml.

The spore suspension is applied with a DeVilbiss atomizer at 8-10 psi air pressure onto the leaf undersurface until fine droplets are formed.

Inoculated seedlings are placed in a humid environment at 60°-62° F. for 40-45 hours, prior to being placed in the greenhouse at 70°-75° F.

Treatment comparisons are made 5-6 days after inoculation. Initially, typical tomato late blight symptoms appear as irregular, greenish-black, water-soaked patches which enlarge and become brown, with a firm corrugated surface. Severe infection will resemble frost damage.

EXAMPLE G

Barley Net Blotch (*Helminthosporium teres*) (BH)

Barley plants (var. Rapidan) are trimmed to a height approximately 2½ inches, 24 hours prior to chemical application. This procedure provides plants of a uniform height and permits rapid inoculation of treated plants.

*Helminthosporium teres* is cultured on potato-dextrose agar (PDA) slants for 14 days at ambient temperature and low light intensity. Spores are harvested by adding deionized water to the PDA slants and scraping the agar surface with a rubber policeman or similar blunt object. The spore suspension is filtered through cheesecloth to remove mycelial and agar fragments and then adjusted to a concentration of $1.5-2.0\times10^5$ spores/ml. One drop (0.05 ml.) of Tween 80 is added to 100 cc inoculum to provide a more even spore distribution on the surface of the barley leaves.

The barley plants are inoculated by spraying the foliage of the plants with a hand sprayer until small droplets of the inoculum are observed on the leaves. Inoculated plants are incubated in a humid environment at 75°-80° F. for 24 hours prior to being placed in the greenhouse at 70°-75° F.

Treatment comparisons are made 6-7 days after inoculation. Typical barley net blotch symptoms initially appear as irregular sunken water-soaked areas which became necrotic as the lesions enlarge.

EXAMPLE H

Cercospora Leafspot of Peanut (*Cercospora arachidicola*) (PC)

Peanut plants (var. Tamnut 74) are 14-days-old when treated.

*Cercospora arachidicola* is cultured on peanut-oatmeal agar (POA) in petri plates for 14 days under fluorescent lights that are 20 cm. above the cultures. These petri plates are inoculated with 0.5 ml. of a spore suspension made in sterile water containing a few drops of Tween 80. The spore suspension is subsequently spread over the surface of the POA plate by means of a sterile glass rod bent in the form of a hockey stick. Spores are harvested from plates by adding deionized water containing a small amount of Tween 80 to the POA plates. The agar surface is filtered through cheesecloth to remove mycelial and agar fragments and then adjusted to a concentration of 2–4×10⁵ spores per ml.

Treated peanut plants are inoculated by spraying the leaves with inoculum until a uniform film of inoculum is observed on the plant. Inoculated plants are incubated in a humid environment at 85°–90° F. for 72 hours. They are removed from the humid environment, allowed to dry, and placed under existing greenhouse conditions.

Treatment comparisons are made 10–14 days after inoculation. Typical Cercospora leafspot are brown to dark circular spots usually surrounded by a yellow halo.

Utilizing these procedures, the results given in Table III below were obtained.

TABLE III

| | Disease Control Level | | | | | | | |
|---|---|---|---|---|---|---|---|---|
| Examples | BH | BOT | BPM | GDM | PC | RB | TLB | WSR |
| 1 | A | E | A | E | A | B | E | A |
| 2 | A | E | A | — | — | E | — | A |
| 3 | A | C | A | C | A | B | C | A |
| 4 | E | E | A | E | — | E | — | A |
| 5 | B | E | A | C | A | E | E | A |
| 6 | A | E | A | E | E | E | E | A |
| 7 | A | C | A | E | A | E | E | A |
| 8 | — | — | A | C | A | E | E | A |

In compiling this table, the following codes are used:
BH = Barley Net Blotch (*Helminthosporium teres*)
BOT = Broad Bean Gray Mold Leaf Spot (*Botrytis fabae*)
BPM = Bean Powdery Mildew (*Erysiphe polygoni*)
GDM = Grape Downy Mildew (*Plasmopora viticola*)
RB = Rice Blast (*Piricularia oryzae*)
PC = Cercospora Leaf Spot of Peanut (*Cercospora arachidicola*)
TLB = Tomato Late Blight (*Phytophthora infestans*)
WSR = Wheat Stem Rust (*Puccinia graminis* f. sp. tritici race 15B-2)

The gamma-butyrolactones, acid addition salts and metal salt complexes of the present invention are useful as agricultural fungicides and as such can be applied to various loci such as the seed, the soil or the foliage. For such purposes these compounds can be used in the technical or pure form as prepared, as solutions or as formulations. The compounds are usually taken up in an agronomically acceptable carrier or are formulated so as to render them suitable for subsequent dissemination as fungicides. For example, these chemical agents can be formulated as wettable powders, emulsifiable concentrates, dusts, granular formulations, aerosols, or flowable emulsion concentrates. In such formulations, the compounds are extended with an agronomically acceptable liquid or solid carrier and, when desired, suitable surfactants are incorporated.

By the term "agronomically acceptable carrier" is meant any substance which can be utilized to dissolve, disperse, or diffuse the chemical agent incorporated therein without impairing the effectiveness of the chemical agent and which does no permanent damage to such environment as the soil, the equipment and the agronomic crops.

It is usually desirable, particularly in the case of foliar spray formulations, to include adjuvants, such as wetting agents, spreading agents, dispersing agents, stickers, adhesives and the like in accordance with the agricultural practices. Such adjuvants commonly used in the art can be found in the John W. McCutcheon, Inc. publication "Detergents and Emulsifiers, Annual."

In general, the compounds of this invention can be dissolved in certain solvents such as acetone, methanol, ethanol, dimethylformamide, pyridine or dimethyl sulfoxide and such solutions can be extended with water. The concentrations of the solutions can vary from about 1% to about 90% with a preferred range being from about 5% to about 50%.

For the preparation of emulsifiable concentrates, the compound can be dissolved in suitable organic solvents, or a mixture of solvents, together with an emulsifying agent which permits dispersion of the fungicide in water. The concentration of the active ingredient in emulsifiable concentrates is usually from about 10% to about 90% and in flowable emulsion concentrates, this can be as high as about 75%.

Wettable powders suitable for spraying, can be prepared by admixing the compounds with a finely divided solid, such as clays, inorganic silicates and carbonates, and silicas and incorporating wetting agents, sticking agents, and/or dispersing agents in such mixtures. The concentration of active ingredients in such formulations is usually in the range of from about 20% to about 98%, preferably from about 40% to about 75%. A typical wettable powder is made by blending 50 parts of 4-ethyl-2-(1-H-imidazoyl)-2-phenyl-gamma-butyrolactone, 45 parts of a synthetic precipitated hydrated silicon dioxide sold under the trademark Hi-Sil®, and 5 parts of sodium lignosulfonate. In another preparation, a kaolin type (Barden) clay is used in place of the Hi-Sil in the above wettable powder, and in another such preparation 25% of the Hi-Sil is replaced with a synthetic sodium silico aluminate sold under the trademark Zeolez®7.

Dusts are prepared by mixing the gamma-butyrolactones and salts and complexes thereof with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing from about 20% to about 80% of the active ingredient are commonly made and are subsequently diluted to from about 1% to about 10% use concentration.

The compounds, salts and complexes of this invention can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and diseases to be controlled, but the preferred effective amount is usually from about 0.1 lb. to about 50 lbs. per acre of the active ingredient.

As a seed protectant, the amount of toxicant coated on the seed is usually at a dosage rate of from about 0.1 to about 20 ounces per hundred pounds of seed. As a soil fungicide, the chemical can be incorporated in the soil or applied to the surface usually at a rate of from about 0.1 to about 50 lbs. per acre. As a foliar fungicide, the toxicant is usually applied to growing plants at a rate of from about 0.25 to about 10 lbs. per acre.

Fungicides which can be combined with the fungicides of this invention include:

(a) dithiocarbamate and derivatives such as: ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), the complex of zineb and polyethylene thiuram disulfide, 3,5-dimethyl-1,3-5-2H-tetrahydrothiadiazine-2-thione (dazomet); and mixtures of these and mixtures with copper salts;

(b) nitrophenol derivatives such as: dinitro-(1-methylheptyl) phenyl crotonate (dinocap), 2-sec-butyl-4,6-dinitrophenyl 3,3-dimethylacrylate (binapacryl), and 2-sec-butyl-4,6-dinitrophenyl isopropyl carbonate;

(c) heterocyclic structures such as: N-trichloromethylthiotetrahydrophthalimide (captan), N-trichloromethylthiophthalimide (folpet), 2-heptadecyl-2-imidazole acetate (glyodine), 2-octylisothiazol-3-one 2,4-dichloro-6-(o-chloroanilino-s-triazine, diethyl phthalimidophosphorothioate, 4-butyl-1,2,4-triazole-5-amino-1-[bis(dimethylamino)phosphinyl]3-phenyl-1,2,4-triazole, 5-ethoxy-3-trichloromethyl-1,2,4-thiadiazole, 2,3-dicyano-1,4-dithiaanthraquinone (dithianon), 2-thio-1,3-dithio-[4,5-b]quinoxaline (thioquinox), methyl 1-(butylcarbamoyl)-2-benzimidazole carbamate (benomyl), 2-(4'-thiazolyl)benzimidazole (thiabendazole), 4-(2-chlorophenylhydrazono)-3-methyl-5-isoxazolone, pyridine-2-thiol-1-oxide, 8-hydroxyquinoline sulfate and metal salts thereof; 2,3-dihydro-5-carboxanilido-6-methyl 1,4-oxathiin-4,4-dioxide-2,3-dihydro-5-carboxanili-do-6-methyl-1,4-oxathiin, alpha-(phenyl-alpha-(2,4-dichlorophenyl)-5-pyridinyl-methanol (triarimol), cis-N-[(1,1,2,2-tetrachloroethyl)-thio]-4-cyclohexene-1,2-dicarboxyimide, 3-[2-(3,5-dimethyl-2-oxycyclohexyl-2-hydroxy]-glutarimide (cycloheximide), dehydroacetic acid, N-(1,1,2,2-tetrachloroethylthio)-3a,4,7,7a-tetrahydrophthalimide (captafol), 5-butyl-2-ethylamino-4-hydroxy-6-methyl-pyrimidine(ethirimol), acetate of 4-cyclododecyl-2,6-dimethylmorpholine (dodemorph), and 6-methyl-2-oxo-1,3-dithiolo[4,5-b]-quinoxaline (quinomethionate).

(d) miscellaneous halogenated fungicides such as: tetrachloro-p-benzoquinone (chloranil), 2,3-dichloro-1,4-naphthoquinone (dichlone), 2,3-dichloro-2,5-dimethoxybenzene (chloroneb), 3,5,6-trichloro-o-anisic acid (tricamba), 2,4,5,6-tetrachloroisophthalo nitrile (TCPN), 2,6-dichloro-4-nitroaniline (dichloran), 2-chloro-1-nitropropane, polychloronitrobenzenes such as: pentachloronitrobenzene (PCNB) and tetrafluorodichloroacetone;

(e) fungicidal antibiotics such as: griseofulvin, kasugamycin and streptomycin;

(f) copper-based fungicides such as: cuprous oxide, basic cupric chloride, basic cupric chloride, basic copper carbonate, copper naphthenate and Bordeaux mixture; and (g) miscellaneous fungicides such as: diphenyl, dodecylguanidine acetate (dodine), phenylmercuric acetate, N-ethylmercuric-1,2,3-6-tetrahydro-3,6-endomethano-3,4,5,6,7,7-hexachlorophthalimide, phenylmercuric monoethanol ammonium lactate, p-dimethylaminobenzenediazo sodium sulfonate, methyl isothiacyanate, 1-thiocyano-2,4-dinitrobenzene, 1-phenylthiosemicarbazide, nickel-containing compounds, calcium cyanamide, lime sulfur, sulfur, and 1,2-bis(3-methoxycarbonyl-2-thioureido) benzene (thiophanatemethyl).

The compounds, acid addition salts and metal salt complexes of this invention can be advantageously employed in various ways. Since these compounds possess broad spectrum fungicidal activity, they can be employed in the storage of cereal grain. These complexes can also be employed as fungicides in turf, fruit orchards, vegetables and golf course applications. Other applications of the compounds of this invention will suggest themselves to those skilled in the art of agriculture and horticulture.

What is claimed is:

1. A compound of the formula:

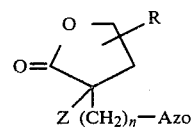

wherein

Z is phenyl or naphthyl, optionally substituted with up to three substituents selected from halogen, nitro, trihalomethyl, cyano, ($C_1$–$C_4$)alkyl, ($C_1$–$C_4$)alkoxy, ($C_1$–$C_4$)alkylthio, ($C_1$–$C_4$)alkylsulfinyl, ($C_1$–$C_4$)alkylsulfonyl, phenyl, benzyl, phenoxy, phenylthio, phenylsulfinyl, or phenylsulfonyl;

R is hydrogen, ($C_1$–$C_{10}$)alkyl, ($C_3$–$C_8$)alkenyl, ($C_3$–$C_8$)alkynyl, or phenyl or naphthyl optionally substituted with up to three substituents selected from halogen, nitro, trihalomethyl, cyano, ($C_1$–$C_4$)alkyl, ($C_1$–$C_4$)alkoxy, ($C_1$–$C_4$)alkylthio, ($C_1$–$C_4$)alkylsulfinyl, ($C_1$–$C_4$)alkylsulfonyl, phenyl, benzyl, phenoxy, phenylthio, phenylsulfinyl, or phenylsulfonyl, or phenyl-($C_1$–$C_4$)alkyl or naphthyl-($C_1$–$C_4$)alkyl the aromatic portion of which is optionally substituted with up to three substituents selected from halogen, nitro, trihalomethyl, cyano, ($C_1$–$C_4$)alkyl, ($C_1$–$C_4$)alkoxy, ($C_1$–$C_4$)alkylthio, ($C_1$–$C_4$)alkylsulfinyl, ($C_1$–$C_4$)alkylsulfonyl, phenyl, benzyl, phenoxy, phenylthio, phenylsulfinyl or phenylsulfonyl;

Azo is 1-$\underline{H}$-imidazoyl, 1-$\underline{H}$-1,2,4-triazoyl or 4-$\underline{H}$-1,2,4-triazoyl;

n is 0 or an integer from 1 to 5;

or an agronomically acceptable acid addition salt or metal salt complex thereof.

2. A compound according to claim 1 wherein Z is a phenyl group substituted with up to three substituents selected from the group consisting of halogen, nitro, trihalomethyl, cyano, ($C_1$ to $C_4$) alkyl, ($C_1$ to $C_4$) alkoxy, ($C_1$ to $C_4$) alkylthio, ($C_1$ to $C_4$) alkylsulfinyl, ($C_1$ to $C_4$) alkylsulfonyl or phenyl, benzyl, phenoxy, phenylthio, phenylsulfinyl or phenylsulfonyl.

3. A compound according to claim 2 wherein Z is phenyl or phenyl substituted with up to two halogen atoms; R is a ($C_1$ to $C_4$) alkyl group; Azo is an imidazoyl or a 1-H-1,2,4-triazoyl group and n is zero or the integer one.

4. A compound according to claim 3 wherein Z is phenyl or 2,4-dichlorophenyl, R is methyl or ethyl, Azo is 1-$\underline{H}$-imidizoyl or 1-$\underline{H}$-1,2,4-triazoyl; and n is zero or the integer one.

5. A compound having the formula:

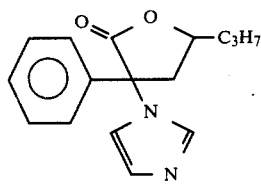

or an agronomically acceptable acid addition salt or a metal salt complex thereof.

6. A compound according to claim 4 having the formula:

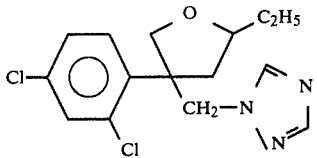

or an agronomically acceptable acid addition salt or a metal salt complex thereof.

7. A fungicidal composition which comprises an agronomically acceptable carrier and as the active ingredient, a fungicidally effective amount of a compound according to claim 1.

8. A method of controlling phytopathogenic fungi which comprises applying to the plant, the plant habitat or the plant seed an effective amount of the compound of claim 1.

9. A method of controlling phytopathogenic fungi which comprises applying to the plant, the plant habitat or the plant seed an effective amount of the compound according to claim 4.

* * * * *

UNITED STATES PATENT AND TRADEMARK OFFICE
CERTIFICATE OF CORRECTION

PATENT NO. : 4,351,839

DATED : September 28, 1982

INVENTOR(S) : HAK-FOON CHAN

It is certified that error appears in the above-identified patent and that said Letters Patent is hereby corrected as shown below:

Col. 7, line 7 "(M, 8H)" should be — (m, 8H) —

Col. 14, line 29 "Zeolez® 7" should be — Zeolex® 7 —

Signed and Sealed this

Twenty-first Day of August 1984

[SEAL]

Attest:

GERALD J. MOSSINGHOFF

Attesting Officer — Commissioner of Patents and Trademarks